(12) United States Patent
Ducray et al.

(10) Patent No.: US 7,700,656 B2
(45) Date of Patent: *Apr. 20, 2010

(54) ORGANIC COMPOUNDS

(75) Inventors: Pierre Ducray, Village-Neuf (FR); Jacques Bouvier, Neuchatel (CH)

(73) Assignee: Novartis AG, Basel (CH)

( * ) Notice: Subject to any disclaimer, the term of this patent is extended or adjusted under 35 U.S.C. 154(b) by 522 days.

This patent is subject to a terminal disclaimer.

(21) Appl. No.: 10/433,811

(22) PCT Filed: Dec. 18, 2001

(86) PCT No.: PCT/EP01/14926

§ 371 (c)(1), (2), (4) Date: Jun. 6, 2003

(87) PCT Pub. No.: WO02/49641

PCT Pub. Date: Jun. 27, 2002

(65) Prior Publication Data

US 2004/0082624 A1    Apr. 29, 2004

(30) Foreign Application Priority Data

Dec. 20, 2000  (CH) .................................. 2489/00

(51) Int. Cl.
    *A01N 37/18*    (2006.01)
(52) U.S. Cl. ..................................... 514/622; 424/405

(58) Field of Classification Search .................. None
See application file for complete search history.

(56) References Cited

U.S. PATENT DOCUMENTS

| | | | |
|---|---|---|---|
| 3,457,294 A | 7/1969 | Crovetti et al. | |
| 4,515,731 A | 5/1985 | Bachman et al. | |
| 5,360,806 A | 11/1994 | Toki et al. | |
| 6,239,077 B1 | 5/2001 | Andoh et al. | |
| 7,153,814 B2 * | 12/2006 | Ducray et al. | ............... 504/312 |

FOREIGN PATENT DOCUMENTS

| | | | |
|---|---|---|---|
| EP | 0953565 | * | 11/1999 |
| GB | 2177394 | | 1/1987 |
| WO | WO 02/060257 A | | 8/2002 |
| WO | WO 02/092552 A | | 11/2002 |
| WO | WO 02/102155 A | | 12/2002 |
| WO | WO 03/004474 A | | 1/2003 |

OTHER PUBLICATIONS

International Search Report.

* cited by examiner

*Primary Examiner*—Neil Levy

(57) ABSTRACT

The invention relates to the use of aminoacetonitrile compounds of formula (I), wherein $R_1$, $R_2$, $R_3$, $R_4$, $R_8$, $R_9$, A, m and n have the significances given in claim 1, in the control of endoparasites, especially helminths, in warm-blooded productie livestock and domestic animals.

4 Claims, No Drawings

ORGANIC COMPOUNDS

The present invention relates to the use of known aminoacetonitrile compounds in the control of endoparasites, especially helminths, in warm-blooded productive livestock and domestic animals.

Attempts have been made to control helminths, in which the endoparasitic nematodes may be the cause of serious diseases of mammals and poultry, by using a few minor classes of active ingredients, for example milbemycins. However, the active ingredients disclosed up until now in literature cannot always fulfil the requirements regarding potency and activity spectrum. There is therefore a need for active ingredients with improved pesticidal properties. It has now been found that the aminoacetonitrile compounds described here possess outstanding properties against endoparasites.

Aminoacetonitrile compounds with pesticidal, especially insecticidal, activity for the protection of plants are described for example in EP 0 953 565 A2. It has surprisingly been shown that the following selection of compounds of formula I also have exceptionally good activity against endoparasites of warm-blooded animals and are tolerated extremely well by the host animal.

The compounds correspond to the general formula

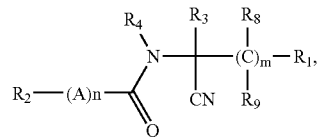

I wherein $R_1$ signifies substituted $C_1$-$C_4$-alkylene, whereby the substituents are selected from the group comprising unsubstituted aryloxy or aryloxy mono- to penta-substituted by $R_5$, and unsubstituted pyridyloxy or pyridyloxy mono- to tetra-substituted by $R_5$, whereby the substituents may be the same as one another or different if the number thereof is greater than 1;

$R_2$ signifies unsubstituted phenyl or phenyl mono- to penta-substituted by $R_5$ or unsubstituted pyridyl or pyridyl mono- to tetra-substituted by $R_5$;

$R_3$ and $R_8$ are either, independently of one another, hydrogen, $C_1$-$C_6$-alkyl or halogen-$C_1$-$C_6$alkyl; or together are $C_2$-$C_6$-alkylene;

$R_4$ signifies hydrogen, $C_1$-$C_6$-alkyl or halogen-$C_1$-$C_6$-alkyl;

$R_5$ signifies $C_1$-$C_6$-alkyl, $C_1$-$C_6$-alkoxy, halogen-$C_1$-$C_6$-alkyl, halogen-$C_1$-$C_6$-alkoxy, $C_2$-$C_6$-alkenyl, halogen-$C_2$-$C_6$-alkenyl, $C_2$-$C_6$-alkinyl, halogen-$C_2$-$C_6$-alkinyl, $C_3$-$C_8$-cycloalkyl, $C_1$-$C_6$-alkylcarbonyl, halogen-$C_1$-$C_6$-alkylcarbonyl, $C_1$-$C_6$-alkoxycarbonyl, halogen-$C_1$-$C_6$-alkoxycarbonyl, $C_1$-$C_6$-alkylsulfonyl, $C_1$-$C_6$-alkylsulfinyl, $C_1$-$C_6$-alkylthio, halogen-$C_1$-$C_6$-alkylthio, phenyl, phenoxy, halogen, cyano or nitro;

A signifies $C(R_6)(R_7)$, CH=CH or C≡C;

$R_6$ and $R_7$ either, independently of one another, signify hydrogen, halogen, $C_1$-$C_6$-alkyl, $C_1$-$C_6$-alkoxy, halogen-$C_1$-$C_6$-alkyl, halogen-$C_1$-$C_6$-alkoxy or $C_3$-$C_6$-cycloalkyl; or together signify $C_2$-$C_6$-alkylene;

$R_9$ is hydrogen or $C_1$-$C_6$-alkyl;

m and n, independently of one other, are 0 or 1;

and optional enantiomers thereof.

Alkyl—as a group per se and as structural element of other groups and compounds such as halogen-alkyl, alkoxy, and alkylthio—is, in each case with due consideration of the specific number of carbon atoms in the group or compound in question, either straight-chained, i.e. methyl, ethyl, propyl, butyl, pentyl, hexyl, heptyl or octyl, or branched, e.g. isopropyl, isobutyl, sec.-butyl, tert.-butyl, isopentyl, neopentyl or isohexyl.

Cycloalkyl—as a group per se and as structural element of other groups and compounds such as halocycloalkyl, cycloalkoxy and cycloalkylthio,—is, in each case with due consideration of the specific number of carbon atoms in the group or compound in question, cyclopropyl, cyclobutyl, cyclopentyl, cyclohexyl, cycloheptyl or cyclooctyl.

Alkenyl—as a group per se and as structural element of other groups and compounds—is, in each case with due consideration of the specific number of carbon atoms in the group or compound in question and of the conjugated or isolated double bonds—either straight-chained, e.g. allyl, 2-butenyl, 3-pentenyl, 1-hexenyl, 1-heptenyl, 1,3-hexadienyl or 1,3-octadienyl, or branched, .g. isopropenyl, isobutenyl, isoprenyl, tert.-pentenyl, isohexenyl, isoheptenyl or isooctenyl.

Alkinyl—as a group per se and as structural element of other groups and compounds—is, in each case with due consideration of the specific number of carbon atoms in the group or compound in question and of the conjugated or isolated double bonds—either straight-chained, e.g. propargyl, 2-butinyl, 3-pentinyl, 1-hexinyl, 1-heptinyl, 3-hexen-1-inyl or 1,5-heptadien-3-inyl, or branched, e.g. 3-methylbut-1-inyl, 4-ethylpent-1-inyl, 4-methylhex-2-inyl or 2-methylhept-3-inyl.

Aryloxy is phenyloxy or 1- or 2-naphthyloxy.

As a rule, halogen signifies fluorine, chlorine, bromine or iodine. The same applies to halogen in combination with other significances, such as halogenalkyl or halogenphenyl.

Halogen-substituted carbon-containing groups and compounds may be partially halogenated or perhalogenated, whereby in the case of multiple halogenation, the halogen substituents may be identical or different. Examples of halogen-alkyl—as a group per se and as structural element of other groups and compounds such as halogen-alkoxy or halogen-alkylthio,—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; pentyl or one of its isomers substituted one to eleven times by fluorine, chlorine and/or bromine, such as $CF(CF_3)(CHF)_2CF_3$ or $CH_2(CF_2)_3CF_3$; and hexyl or one of its isomers substituted one to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Alkoxy groups preferably have a chain length of 1 to 6 carbon atoms. Alkoxy is for example methoxy, ethoxy, propoxy, isopropoxy, n-butoxy, isobutoxy, sec.-butoxy and tert.-butoxy, as well as the isomers pentyloxy and hexyloxy; preferably methoxy and ethoxy. Halogenalkoxy groups preferably have a chain length of 1 to 6 carbon atoms. Halogenalkoxy is e.g. fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Preferred embodiments within the scope of the invention are:

(1) A compound of formula I, wherein $R_1$ is substituted $C_1$-$C_4$-alkylene, whereby the substituents are selected from the group comprising unsubstituted phenyloxy or phenyloxy mono- to tri-substituted by $R_5$, whereby the substituents may be identical or different if the number thereof is greater than 1; in particular substituted $C_1$-$C_2$-alkylene, whereby the substituents are selected from the group comprising unsubstituted phenyloxy or phenyloxy mono- to tri-substituted by $R_5$, whereby the substituents may be identical or different if the number thereof is greater than 1; most particularly substituted methylene, whereby the substituents are selected from the group comprising unsubstituted phenyloxy or phenyloxy mono- to di-substituted by $R_5$, whereby the substituents may be identical or different if the number thereof is greater than 1;

(2) A compound of formula I, wherein $R_2$ is unsubstituted phenyl or phenyl mono- to penta-substituted by $R_5$; in particular phenyl mono- to tri-substituted by $R_5$; most particularly phenyl mono- to di-substituted by $R_5$;

(3) A compound of formula I, wherein $R_3$ is hydrogen or $C_1$-$C_6$-alkyl; particularly hydrogen or $C_1$-$C_4$-alkyl; most particularly methyl;

(4) A compound of formula I, wherein $R_4$ is hydrogen or $C_1$-$C_6$-alkyl; particularly hydrogen or $C_1$-$C_2$-alkyl; most particularly hydrogen;

(5) A compound of formula I, wherein $R_5$ is $C_1$-$C_6$-alkyl, $C_1$-$C_6$-alkoxy, halogen-$C_1$-$C_6$-alkyl, halogen-$C_1$-$C_6$-alkoxy, $C_2$-$C_6$-alkenyl, halogen-$C_2$-$C_6$-alkenyl, $C_2$-$C_6$-alkinyl, halogen-$C_2$-$C_6$-alkinyl, $C_3$-$C_8$-cycloalkyl, $C_1$-$C_6$-alkylcarbonyl, halogen-$C_1$-$C_6$-alkylcarbonyl, $C_1$-$C_6$-alkoxycarbonyl, halogen-$C_1$-$C_6$-alkoxycarbonyl, $C_1$-$C_6$-alkylsulfonyl, $C_1$-$C_6$-alkylsulfinyl, halogen, cyano oder nitro; especially $C_1$-$C_4$-alkyl, $C_1$-$C_4$-alkoxy, halogen-$C_1$-$C_4$-alkyl, halogen-$C_1$-$C_4$-alkoxy, halogen, cyano or nitro; most preferably $C_1$-$C_4$-alkyl, halogen-$C_1$-$C_2$-alkyl, halogen, cyano or nitro; especially halogen-$C_1$-$C_2$-alkyl or halogen;

(6) A compound of formula I, in which A is $C(R_6)(R_7)$ or CH=CH; especially $C(R_6)(R_7)$;

(7) A compound of formula I, wherein $R_6$ and $R_7$ are either, independently of one another, hydrogen, $C_1$-$C_4$-alkyl, or $C_3$-$C_6$-cycloalkyl; or together are $C_2$-$C_6$-alkylene; especially, independently of one another, hydrogen or $C_1$-$C_2$-alkyl; most particularly hydrogen;

(8) A compound of formula I, wherein $R_8$ is hydrogen or $C_1$-$C_6$-alkyl; particularly hydrogen or $C_1$-$C_4$-alkyl; most particularly hydrogen;

(9) A compound of formula I, wherein $R_9$ is hydrogen or $C_1$-$C_4$-alkyl; particularly hydrogen or $C_1$-$C_2$-alkyl; most particularly hydrogen;

(10) A compound of formula I, wherein m is 0;

(11) A compound of formula I, wherein n is 1;

(12) A compound of formula I, wherein $R_1$ is substituted $C_1$-$C_4$-alkylene, whereby the substituents are selected from the group comprising unsubstituted phenyloxy or phenyloxy mono- to tri-substituted by $R_5$, whereby the substituents may be identical or different if the number thereof is greater than 1; $R_2$ is unsubstituted phenyl or phenyl mono- to penta-substituted by $R_5$; $R_3$ is hydrogen or $C_1$-$C_6$-alkyl; $R_4$ is hydrogen or $C_1$-$C_6$-alkyl; $R_5$ is $C_1$-$C_4$-alkyl, $C_1$-$C_4$-alkoxy, halogen-$C_1$-$C_4$-alkyl, halogen-$C_1$-$C_4$-alkoxy, halogen, cyano or nitro; A is $C(R_6)(R_7)$ or CH=CH; $R_6$ and $R_7$ are either, independently of one another, hydrogen, $C_1$-$C_4$-alkyl, or $C_3$-$C_6$-cycloalkyl, or together are $C_2$-$C_6$-alkylene; $R_8$ is hydrogen or $C_1$-$C_6$-alkyl; m is 0 and n is 1;

(13) A compound of formula I, wherein $R_1$ is substituted $C_1$-$C_2$-alkylene, whereby the substituents are selected from the group comprising unsubstituted phenyloxy or phenyloxy mono- to tri-substituted by $R_5$, whereby the substituents may be identical or different if the number thereof is greater than 1; $R_2$ is phenyl mono- to tri-substituted by $R_5$; $R_3$ is hydrogen or $C_1$-$C_4$-alkyl; $R_4$ is hydrogen or $C_1$-$C_2$-alkyl; $R_5$ is $C_1$-$C_2$-alkyl, halogen-$C_1$-$C_2$-alkyl, halogen, cyano or nitro; A is $C(R_6)(R_7)$; $R_6$ and $R_7$ are, independently of one another, hydrogen or $C_1$-$C_2$-alkyl; $R_8$ is hydrogen or $C_1$-$C_6$-alkyl; m is 0 and n is 1; and

(14) A compound of formula I, wherein $R_1$ is substituted methylene, whereby the substituents are selected from the group comprising unsubstituted phenyloxy or phenyloxy mono- to di-substituted by $R_5$, whereby the substituents may be identical or different if the number thereof is greater than 1; $R_2$ is phenyl mono- to di-substituted by $R_5$; $R_3$ is methyl, $R_4$ is hydrogen, $R_5$ is halogen-$C_1$-$C_2$-alkyl or halogen; A is $C(R_6)(R_7)$; $R_6$, $R_7$ and $R_8$ are hydrogen, m is 0 and n is 1.

The compounds of formula I named in the following Table 1 are preferred in particular.

The compounds I may be present in the form of one of the possible isomers or as a mixture thereof, e.g. depending on the number, absolute and relative configurations of the asymmetric carbon atoms as pure isomers, such as antipodes and/or diastereoisomers, or as isomeric mixtures, such as enantiomeric mixtures, e.g. racemates, diastereoisomeric mixtures or racemic mixtures; the invention relates to both the pure isomers and all the possible isomeric mixtures, and is to be understood as such hereinbefore and hereinafter, even if stereochemical details are not specifically mentioned in each case.

Synthesis of the compounds is described for example in EP 0 953 565 A2.

TABLE 1

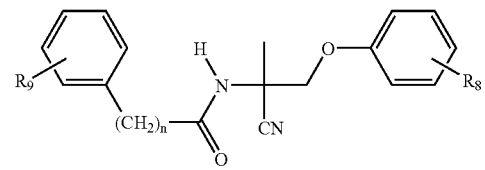

| No. | n | $R_8$ | $R_9$ | phys. data |
|-----|---|-------|-------|------------|
| 1.1 | 0 | 2-Cl | 2-Cl | |
| 1.2 | 0 | 2-Cl | 3-Cl | |
| 1.3 | 0 | 2-Cl | 4-Cl | m.p. 137-9° |
| 1.4 | 0 | 2-Cl | 2,3-Cl$_2$ | |
| 1.5 | 0 | 2-Cl | 2,4-Cl$_2$ | |
| 1.6 | 0 | 2-Cl | 2,5-Cl$_2$ | |
| 1.7 | 0 | 2-Cl | 2,6-Cl$_2$ | m.p. 178-80° |
| 1.8 | 0 | 2-Cl | 3,4-Cl$_2$ | |
| 1.9 | 0 | 2-Cl | 3,5-Cl$_2$ | |
| 1.10 | 0 | 2-Cl | 2-CF$_3$ | m.p. 47-49° |
| 1.11 | 0 | 2-Cl | 3-CF$_3$ | |
| 1.12 | 0 | 2-Cl | 4-CF$_3$ | m.p. 131-3° |

TABLE 1-continued

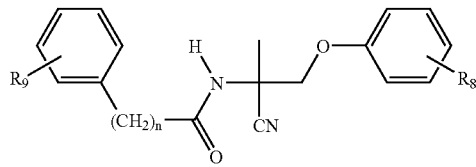

| No. | n | R8 | R9 | phys. data |
|---|---|---|---|---|
| 1.13 | 0 | 3-Cl | 2-Cl | |
| 1.14 | 0 | 3-Cl | 3-Cl | |
| 1.15 | 0 | 3-Cl | 4-Cl | |
| 1.16 | 0 | 3-Cl | 2,3-Cl2 | |
| 1.17 | 0 | 3-Cl | 2,4-Cl2 | |
| 1.18 | 0 | 3-Cl | 2,5-Cl2 | |
| 1.19 | 0 | 3-Cl | 2,6-Cl2 | |
| 1.20 | 0 | 3-Cl | 3,4-Cl2 | |
| 1.21 | 0 | 3-Cl | 3,5-Cl2 | |
| 1.22 | 0 | 3-Cl | 2-CF3 | |
| 1.23 | 0 | 3-Cl | 3-CF3 | |
| 1.24 | 0 | 3-Cl | 4-CF3 | |
| 1.25 | 0 | 4-Cl | 2-Cl | |
| 1.26 | 0 | 4-Cl | 3-Cl | |
| 1.27 | 0 | 4-Cl | 4-Cl | |
| 1.28 | 0 | 4-Cl | 2,3-Cl2 | |
| 1.29 | 0 | 4-Cl | 2,4-Cl2 | |
| 1.30 | 0 | 4-Cl | 2,5-Cl2 | |
| 1.31 | 0 | 4-Cl | 2,6-Cl2 | |
| 1.32 | 0 | 4-Cl | 3,4-Cl2 | |
| 1.33 | 0 | 4-Cl | 3,5-Cl2 | |
| 1.34 | 0 | 4-Cl | 2-CF3 | |
| 1.35 | 0 | 4-Cl | 3-CF3 | |
| 1.36 | 0 | 4-Cl | 4-CF3 | |
| 1.37 | 0 | 2,3-Cl2 | 2-Cl | |
| 1.38 | 0 | 2,3-Cl2 | 3-Cl | |
| 1.39 | 0 | 2,3-Cl2 | 4-Cl | m.p. 190-2° |
| 1.40 | 0 | 2,3-Cl2 | 2,3-Cl2 | |
| 1.41 | 0 | 2,3-Cl2 | 2,4-Cl2 | |
| 1.42 | 0 | 2,3-Cl2 | 2,5-Cl2 | |
| 1.43 | 0 | 2,3-Cl2 | 2,6-Cl2 | |
| 1.44 | 0 | 2,3-Cl2 | 3,4-Cl2 | |
| 1.45 | 0 | 2,3-Cl2 | 3,5-Cl2 | |
| 1.46 | 0 | 2,3-Cl2 | 2-CF3 | |
| 1.47 | 0 | 2,3-Cl2 | 3-CF3 | |
| 1.48 | 0 | 2,3-Cl2 | 4-CF3 | m.p. 155-7° |
| 1.49 | 0 | 2,4-Cl2 | 2-Cl | |
| 1.50 | 0 | 2,4-Cl2 | 3-Cl | m.p. 122-3° |
| 1.51 | 0 | 2,4-Cl2 | 4-Cl | m.p. 143-5° |
| 1.52 | 0 | 2,4-Cl2 | 2,3-Cl2 | |
| 1.53 | 0 | 2,4-Cl2 | 2,4-Cl2 | |
| 1.54 | 0 | 2,4-Cl2 | 2,5-Cl2 | |
| 1.55 | 0 | 2,4-Cl2 | 2,6-Cl2 | |
| 1.56 | 0 | 2,4-Cl2 | 3,4-Cl2 | |
| 1.57 | 0 | 2,4-Cl2 | 3,5-Cl2 | |
| 1.58 | 0 | 2,4-Cl2 | 2-CF3 | |
| 1.59 | 0 | 2,4-Cl2 | 3-CF3 | |
| 1.60 | 0 | 2,4-Cl2 | 4-CF2 | m.p. 99-102° |
| 1.61 | 0 | 2,5-Cl2 | 2-Cl | |
| 1.62 | 0 | 2,5-Cl2 | 3-Cl | |
| 1.63 | 0 | 2,5-Cl2 | 4-Cl | |
| 1.64 | 0 | 2,5-Cl2 | 2,3-Cl2 | |
| 1.65 | 0 | 2,5-Cl2 | 2,4-Cl2 | |
| 1.66 | 0 | 2,5-Cl2 | 2,5-Cl2 | |
| 1.67 | 0 | 2,5-Cl2 | 2,6-Cl2 | |
| 1.68 | 0 | 2,5-Cl2 | 3,4-Cl2 | |
| 1.69 | 0 | 2,5-Cl2 | 3,5-Cl2 | |
| 1.70 | 0 | 2,5-Cl2 | 2-CF3 | |
| 1.71 | 0 | 2,5-Cl2 | 3-CF3 | |
| 1.72 | 0 | 2,5-Cl2 | 4-CF3 | |
| 1.73 | 0 | 2,6-Cl2 | 2-Cl | |
| 1.74 | 0 | 2,6-Cl2 | 3-Cl | |
| 1.75 | 0 | 2,6-Cl2 | 4-Cl | |
| 1.76 | 0 | 2,6-Cl2 | 2,3-Cl2 | |
| 1.77 | 0 | 2,6-Cl2 | 2,4-Cl2 | |
| 1.78 | 0 | 2,6-Cl2 | 2,5-Cl2 | |
| 1.79 | 0 | 2,6-Cl2 | 2,6-Cl2 | |
| 1.80 | 0 | 2,6-Cl2 | 3,4-Cl2 | |

TABLE 1-continued

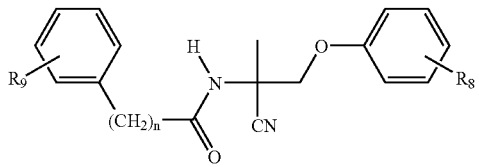

| No. | n | R8 | R9 | phys. data |
|---|---|---|---|---|
| 1.81 | 0 | 2,6-Cl2 | 3,5-Cl2 | |
| 1.82 | 0 | 2,6-Cl2 | 2-CF3 | |
| 1.83 | 0 | 2,6-Cl2 | 3-CF3 | |
| 1.84 | 0 | 2,6-Cl2 | 4-CF3 | |
| 1.85 | 0 | 3,4-Cl2 | 2-Cl | |
| 1.86 | 0 | 3,4-Cl2 | 3-Cl | |
| 1.87 | 0 | 3,4-Cl2 | 4-Cl | |
| 1.88 | 0 | 3,4-Cl2 | 2,3-Cl2 | |
| 1.89 | 0 | 3,4-Cl2 | 2,4-Cl2 | |
| 1.90 | 0 | 3,4-Cl2 | 2,5-Cl2 | |
| 1.91 | 0 | 3,4-Cl2 | 2,6-Cl2 | |
| 1.92 | 0 | 3,4-Cl2 | 3,4-Cl2 | |
| 1.93 | 0 | 3,4-Cl2 | 3,5-Cl2 | |
| 1.94 | 0 | 3,4-Cl2 | 2-CF3 | |
| 1.95 | 0 | 3,4-Cl2 | 3-CF3 | |
| 1.96 | 0 | 3,4-Cl2 | 4-CF3 | m.p. 93-5° |
| 1.97 | 0 | 3,5-Cl2 | 2-Cl | |
| 1.98 | 0 | 3,5-Cl2 | 3-Cl | |
| 1.99 | 0 | 3,5-Cl2 | 4-Cl | |
| 1.100 | 0 | 3,5-Cl2 | 2,3-Cl2 | |
| 1.101 | 0 | 3,5-Cl2 | 2,4-Cl2 | |
| 1.102 | 0 | 3,5-Cl2 | 2,5-Cl2 | |
| 1.103 | 0 | 3,5-Cl2 | 2,6-Cl2 | |
| 1.104 | 0 | 3,5-Cl2 | 3,4-Cl2 | |
| 1.105 | 0 | 3,5-Cl2 | 3,5-Cl2 | |
| 1.106 | 0 | 3,5-Cl2 | 2-CF3 | |
| 1.107 | 0 | 3,5-Cl2 | 3-CF3 | |
| 1.108 | 0 | 3,5-Cl2 | 4-CF3 | |
| 1.109 | 0 | 2-CF3 | 2-Cl | |
| 1.110 | 0 | 2-CF3 | 3-Cl | |
| 1.111 | 0 | 2-CF3 | 4-Cl | |
| 1.112 | 0 | 2-CF3 | 2,3-Cl2 | |
| 1.113 | 0 | 2-CF3 | 2,4-Cl2 | |
| 1.114 | 0 | 2-CF3 | 2,5-Cl2 | |
| 1.115 | 0 | 2-CF3 | 2,6-Cl2 | m.p. 168-70° |
| 1.116 | 0 | 2-CF3 | 3,4-Cl2 | |
| 1.117 | 0 | 2-CF3 | 3,5-Cl2 | |
| 1.118 | 0 | 2-CF3 | 2-CF3 | |
| 1.119 | 0 | 2-CF3 | 3-CF3 | |
| 1.120 | 0 | 2-CF3 | 4-CF3 | m.p. 148.5° |
| 1.121 | 0 | 3-CF3 | 2-Cl | |
| 1.122 | 0 | 3-CF3 | 3-Cl | |
| 1.123 | 0 | 3-CF3 | 4-Cl | |
| 1.124 | 0 | 3-CF3 | 2,3-Cl2 | |
| 1.125 | 0 | 3-CF3 | 2,4-Cl2 | |
| 1.126 | 0 | 3-CF3 | 2,5-Cl2 | |
| 1.127 | 0 | 3-CF3 | 2,6-Cl2 | |
| 1.128 | 0 | 3-CF3 | 3,4-Cl2 | |
| 1.129 | 0 | 3-CF3 | 3,5-Cl2 | |
| 1.130 | 0 | 3-CF3 | 2-CF3 | |
| 1.131 | 0 | 3-CF3 | 3-CF3 | |
| 1.132 | 0 | 3-CF3 | 4-CF3 | |
| 1.133 | 0 | 4-CF3 | 2-Cl | |
| 1.134 | 0 | 4-CF3 | 3-Cl | m.p. 160-2° |
| 1.135 | 0 | 4-CF3 | 4-Cl | m.p. 147-9° |
| 1.136 | 0 | 4-CF3 | 2,3-Cl2 | |
| 1.137 | 0 | 4-CF3 | 2,4-Cl2 | |
| 1.138 | 0 | 4-CF3 | 2,5-Cl2 | |
| 1.139 | 0 | 4-CF3 | 2,6-Cl2 | |
| 1.140 | 0 | 4-CF3 | 3,4-Cl2 | |
| 1.141 | 0 | 4-CF3 | 3,5-Cl2 | |
| 1.142 | 0 | 4-CF3 | 2-CF3 | |
| 1.143 | 0 | 4-CF3 | 3-CF3 | |
| 1.144 | 0 | 4-CF3 | 4-CF3 | m.p. 140-3° |
| 1.145 | 1 | 2-Cl | 2-Cl | |
| 1.146 | 1 | 2-Cl | 3-Cl | |
| 1.147 | 1 | 2-Cl | 4-Cl | |
| 1.148 | 1 | 2-Cl | 2,3-Cl2 | |

TABLE 1-continued

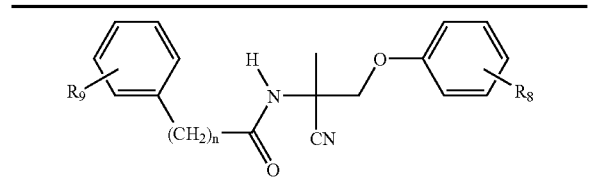

| No. | n | R8 | R9 | phys. data |
|---|---|---|---|---|
| 1.149 | 1 | 2-Cl | 2,4-Cl₂ | |
| 1.150 | 1 | 2-Cl | 2,5-Cl₂ | |
| 1.151 | 1 | 2-Cl | 2,6-Cl₂ | |
| 1.152 | 1 | 2-Cl | 3,4-Cl₂ | |
| 1.153 | 1 | 2-Cl | 3,5-Cl₂ | |
| 1.154 | 1 | 2-Cl | 2-CF₃ | |
| 1.155 | 1 | 2-Cl | 3-CF₃ | |
| 1.156 | 1 | 2-Cl | 4-CF₃ | |
| 1.157 | 1 | 3-Cl | 2-Cl | |
| 1.158 | 1 | 3-Cl | 3-Cl | |
| 1.159 | 1 | 3-Cl | 4-Cl | |
| 1.160 | 1 | 3-Cl | 2,3-Cl₂ | |
| 1.161 | 1 | 3-Cl | 2,4-Cl₂ | |
| 1.162 | 1 | 3-Cl | 2,5-Cl₂ | |
| 1.163 | 1 | 3-Cl | 2,6-Cl₂ | |
| 1.164 | 1 | 3-Cl | 3,4-Cl₂ | |
| 1.165 | 1 | 3-Cl | 3,5-Cl₂ | |
| 1.166 | 1 | 3-Cl | 2-CF₃ | |
| 1.167 | 1 | 3-Cl | 3-CF₃ | |
| 1.168 | 1 | 3-Cl | 4-CF₃ | |
| 1.169 | 1 | 4-Cl | 2-Cl | |
| 1.170 | 1 | 4-Cl | 3-Cl | |
| 1.171 | 1 | 4-Cl | 4-Cl | |
| 1.172 | 1 | 4-Cl | 2,3-Cl₂ | |
| 1.173 | 1 | 4-Cl | 2,4-Cl₂ | |
| 1.174 | 1 | 4-Cl | 2,5-Cl₂ | |
| 1.175 | 1 | 4-Cl | 2,6-Cl₂ | |
| 1.176 | 1 | 4-Cl | 3,4-Cl₂ | |
| 1.177 | 1 | 4-Cl | 3,5-Cl₂ | |
| 1.178 | 1 | 4-Cl | 2-CF₃ | |
| 1.179 | 1 | 4-Cl | 3-CF₃ | |
| 1.180 | 1 | 4-Cl | 4-CF₃ | |
| 1.181 | 1 | 2,3-Cl₂ | 2-Cl | |
| 1.182 | 1 | 2,3-Cl₂ | 3-Cl | |
| 1.183 | 1 | 2,3-Cl₂ | 4-Cl | |
| 1.184 | 1 | 2,3-Cl₂ | 2,3-Cl₂ | |
| 1.185 | 1 | 2,3-Cl₂ | 2,4-Cl₂ | |
| 1.186 | 1 | 2,3-Cl₂ | 2,5-Cl₂ | |
| 1.187 | 1 | 2,3-Cl₂ | 2,6-Cl₂ | |
| 1.188 | 1 | 2,3-Cl₂ | 3,4-Cl₂ | |
| 1.189 | 1 | 2,3-Cl₂ | 3,5-Cl₂ | |
| 1.190 | 1 | 2,3-Cl₂ | 2-CF₃ | |
| 1.191 | 1 | 2,3-Cl₂ | 3-CF₃ | |
| 1.192 | 1 | 2,3-Cl₂ | 4-CF₃ | |
| 1.193 | 1 | 2,4-Cl₂ | 2-Cl | |
| 1.194 | 1 | 2,4-Cl₂ | 3-Cl | m.p. 151-3° |
| 1.195 | 1 | 2,4-Cl₂ | 4-Cl | m.p. 102-4° |
| 1.196 | 1 | 2,4-Cl₂ | 2,3-Cl₂ | |
| 1.197 | 1 | 2,4-Cl₂ | 2,4-Cl₂ | |
| 1.198 | 1 | 2,4-Cl₂ | 2,5-Cl₂ | |
| 1.199 | 1 | 2,4-Cl₂ | 2,6-Cl₂ | |
| 1.200 | 1 | 2,4-Cl₂ | 3,4-Cl₂ | |
| 1.201 | 1 | 2,4-Cl₂ | 3,5-Cl₂ | |
| 1.202 | 1 | 2,4-Cl₂ | 2-CF₃ | |
| 1.203 | 1 | 2,4-Cl₂ | 3-CF₃ | |
| 1.204 | 1 | 2,4-Cl₂ | 4-CF₃ | m.p. 94-6° |
| 1.205 | 1 | 2,5-Cl₂ | 2-Cl | |
| 1.206 | 1 | 2,5-Cl₂ | 3-Cl | |
| 1.207 | 1 | 2,5-Cl₂ | 4-Cl | |
| 1.208 | 1 | 2,5-Cl₂ | 2,3-Cl₂ | |
| 1.209 | 1 | 2,5-Cl₂ | 2,4-Cl₂ | |
| 1.210 | 1 | 2,5-Cl₂ | 2,5-Cl₂ | |
| 1.211 | 1 | 2,5-Cl₂ | 2,6-Cl₂ | |
| 1.212 | 1 | 2,5-Cl₂ | 3,4-Cl₂ | |
| 1.213 | 1 | 2,5-Cl₂ | 3,5-Cl₂ | |
| 1.214 | 1 | 2,5-Cl₂ | 2-CF₃ | |
| 1.215 | 1 | 2,5-Cl₂ | 3-CF₃ | |
| 1.216 | 1 | 2,5-Cl₂ | 4-CF₃ | |
| 1.217 | 1 | 2,6-Cl₂ | 2-Cl | |
| 1.218 | 1 | 2,6-Cl₂ | 3-Cl | |
| 1.219 | 1 | 2,6-Cl₂ | 4-Cl | |
| 1.220 | 1 | 2,6-Cl₂ | 2,3-Cl₂ | |
| 1.221 | 1 | 2,6-Cl₂ | 2,4-Cl₂ | |
| 1.222 | 1 | 2,6-Cl₂ | 2,5-Cl₂ | |
| 1.223 | 1 | 2,6-Cl₂ | 2,6-Cl₂ | |
| 1.224 | 1 | 2,6-Cl₂ | 3,4-Cl₂ | |
| 1.225 | 1 | 2,6-Cl₂ | 3,5-Cl₂ | |
| 1.226 | 1 | 2,6-Cl₂ | 2-OF₃ | |
| 1.227 | 1 | 2,6-Cl₂ | 3-CF₃ | |
| 1.228 | 1 | 2,6-Cl₂ | 4-OF₃ | |
| 1.229 | 1 | 3,4-Cl₂ | 2-Cl | |
| 1.230 | 1 | 3,4-Cl₂ | 3-Cl | |
| 1.231 | 1 | 3,4-Cl₂ | 4-Cl | |
| 1.232 | 1 | 3,4-Cl₂ | 2,3-Cl₂ | |
| 1.233 | 1 | 3,4-Cl₂ | 2,4-Cl₂ | |
| 1.234 | 1 | 3,4-Cl₂ | 2,5-Cl₂ | |
| 1.235 | 1 | 3,4-Cl₂ | 2,6-Cl₂ | |
| 1.236 | 1 | 3,4-Cl₂ | 3,4-Cl₂ | |
| 1.237 | 1 | 3,4-Cl₂ | 3,5-Cl₂ | |
| 1.238 | 1 | 3,4-Cl₂ | 2-CF₃ | |
| 1.239 | 1 | 3,4-Cl₂ | 3-0 F3 | |
| 1.240 | 1 | 3,4-Cl₂ | 4-OF₃ | |
| 1.241 | 1 | 3,5-Cl₂ | 2-Cl | |
| 1.242 | 1 | 3,5-Cl₂ | 3-Cl | |
| 1.243 | 1 | 3,5-Cl₂ | 4-Cl | |
| 1.244 | 1 | 3,5-Cl₂ | 2,3-Cl₂ | |
| 1.245 | 1 | 3,5-Cl₂ | 2,4-Cl₂ | |
| 1.246 | 1 | 3,5-Cl₂ | 2,5-Cl₂ | |
| 1.247 | 1 | 3,5-Cl₂ | 2,6-Cl₂ | |
| 1.248 | 1 | 3,5-Cl₂ | 3,4-Cl₂ | |
| 1.249 | 1 | 3,5-Cl₂ | 3,5-Cl₂ | |
| 1.250 | 1 | 3,5-Cl₂ | 2-CF₃ | |
| 1.251 | 1 | 3,5-Cl₂ | 3-CF₃ | |
| 1.252 | 1 | 3,5-Cl₂ | 4-CF₃ | |
| 1.253 | 1 | 2-CF₃ | 2-Cl | |
| 1.254 | 1 | 2-CF₃ | 3-Cl | |
| 1.255 | 1 | 2-CF₃ | 4-Cl | |
| 1.256 | 1 | 2-CF₃ | 2,3-Cl₂ | |
| 1.257 | 1 | 2-OF₃ | 2,4-Cl₂ | |
| 1.258 | 1 | 2-CF₃ | 2,5-Cl₂ | |
| 1.259 | 1 | 2-CF₃ | 2,6-Cl₂ | |
| 1.260 | 1 | 2-CF₃ | 3,4-Cl₂ | |
| 1.261 | 1 | 2-CF₃ | 3,5-Cl₂ | |
| 1.262 | 1 | 2-CF₃ | 2-CF₃ | |
| 1.263 | 1 | 2-CF₃ | 3-CF₃ | |
| 1.264 | 1 | 2-CF₃ | 4-CF₃ | |
| 1.265 | 1 | 3-CF₃ | 2-Cl | |
| 1.266 | 1 | 3-CF₃ | 3-Cl | |
| 1.267 | 1 | 3-CF₃ | 4-Cl | |
| 1.268 | 1 | 3-CF₃ | 2,3-Cl₂ | |
| 1.269 | 1 | 3-CF₃ | 2,4-Cl₂ | |
| 1.270 | 1 | 3-CF₃ | 2,5-Cl₂ | |
| 1.271 | 1 | 3-CF₃ | 2,6-Cl₂ | |
| 1.272 | 1 | 3-CF₃ | 3,4-Cl₂ | |
| 1.273 | 1 | 3-CF₃ | 3,5-Cl₂ | |
| 1.274 | 1 | 3-CF₃ | 2-CF₃ | |
| 1.275 | 1 | 3-CF₃ | 3-CF₃ | |
| 1.276 | 1 | 3-CF₃ | 4-CF₃ | |
| 1.277 | 1 | 4-CF₃ | 2-Cl | |
| 1.278 | 1 | 4-CF₃ | 3-Cl | m.p. 136-8° |
| 1.279 | 1 | 4-CF₃ | 4-Cl | m.p. 133-5° |
| 1.280 | 1 | 4-CF₃ | 2,3-Cl₂ | |
| 1.281 | 1 | 4-CF₃ | 2,4-Cl₂ | |
| 1.282 | 1 | 4-CF₃ | 2,5-Cl₂ | |
| 1.283 | 1 | 4-CF₃ | 2,6-Cl₂ | |
| 1.284 | 1 | 4-CF₃ | 3,4-Cl₂ | |

TABLE 1-continued

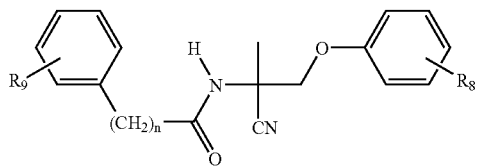

| No. | n | $R_8$ | $R_9$ | phys. data |
|---|---|---|---|---|
| 1.285 | 1 | 4-$CF_3$ | 3,5-$Cl_2$ | |
| 1.286 | 1 | 4-$CF_3$ | 2-$CF_3$ | |
| 1.287 | 1 | 4-$CF_3$ | 3-$CF_3$ | |
| 1.288 | 1 | 4-$CF_3$ | 4-$CF_3$ | m.p. 126-8° |

TABLE 2

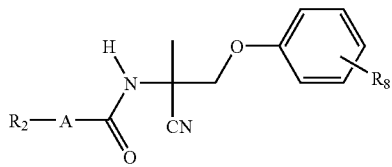

| No. | A | $R_8$ | $R_2$ | phys. data |
|---|---|---|---|---|
| 2.1 | — | H | $C_6H_4$-4-$CF_3$ | m.p. 137° |
| 2.2 | — | 2-F | $C_6H_4$-4-$CF_3$ | m.p. 155° |
| 2.3 | — | 2-Cl | $C_6H_4$-2-F | |
| 2.4 | — | 2-Cl | $C_6H_4$-4-F | |
| 2.5 | — | 2-Cl | $C_6H_4$-4-$CH_3$ | |
| 2.6 | — | 2-Cl | $C_6H_4$-4-C(O)$CH_3$ | m.p. 135-7° |
| 2.7 | — | 2-Cl | $C_6H_3$-2,6-$F_2$ | m.p. 108-11° |
| 2.8 | — | 2-Cl | $C_6H_3$-2-F-4-$CF_3$ | |
| 2.9 | — | 2-$CF_3$ | $C_6H_3$-2,6-$F_2$ | m.p. 40-4° |
| 2.10 | — | 2-$CF_3$ | $C_6H_4$-4-$CH_3$ | m.p. 147-50° |
| 2.11 | — | 2-$CF_3$ | $C_6H_4$-4-t-$C_4H_9$ | m.p. 160-3° |
| 2.12 | — | 2-$CF_3$ | $C_6H_4$-4-$OCH_3$ | m.p. 180-2° |
| 2.13 | — | 2-$CF_3$ | $C_6H_4$-4-$OC_6H_5$ | m.p. 45-9° |
| 2.14 | — | 2-$CF_3$ | $C_6H_4$-4-$SCF_3$ | m.p. 78-82° |
| 2.15 | — | 2-$CF_3$ | $C_6H_4$-4-C(O)$OCH_3$ | m.p. 144-6° |
| 2.16 | — | 2-$CF_3$ | $C_6H_4$-4-C(O)$CF_3$ | m.p. 52-6° |
| 2.17 | — | 2-$CF_3$ | $C_6H_4$-4-$C_6H_5$ | m.p. 137-40° |
| 2.18 | — | 2-$CF_3$ | $C_6H_3$-2,4-$(CF_3)_2$ | m.p. 49-52° |
| 2.19 | — | 2-$CF_3$ | $C_6H_3$-2-F-4-$CF_3$ | |
| 2.20 | — | 2-$CF_3$ | $C_6H_3$-3-F-4-$CF_3$ | m.p. 149-50° |
| 2.21 | — | 2-$CF_3$ | 3-$C_5H_3$N-6-Cl | m.p. 138-40° |
| 2.22 | — | 2-$OCH_3$ | $C_6H_4$-4-$CF_3$ | m.p. 86° |
| 2.23 | — | 2-$OCF_3$ | $C_6H_4$-4-$CF_3$ | m.p. 105° |
| 2.24 | — | 4-S($O_2$)$CH_3$ | $C_6H_4$-4-$CF_3$ | |
| 2.25 | — | 2-C(O)$OCH_3$ | $C_6H_4$-4-$CF_3$ | m.p. 118° |
| 2.26 | — | 2,4-$F_2$ | $C_6H_4$-4-$CF_3$ | m.p. 130° |
| 2.27 | — | 2,5-$F_2$ | $C_6H_4$-4-$CF_3$ | m.p. 125° |
| 2.28 | — | 2,5-$Cl_2$ | $C_6H_4$-4-$CF_3$ | m.p. 140° |
| 2.29 | — | 2-Cl, 4-$CH_3$ | $C_6H_4$-4-$CF_3$ | m.p. 133° |
| 2.30 | — | 2-Cl, 5-$CH_3$ | $C_6H_4$-4-C(O)$CF_3$ | m.p. 46-50° |
| 2.31 | — | 2-Cl, 5-$CH_3$ | $C_6H_4$-4-$CF_3$ | m.p. 141° |
| 2.32 | — | 2-Cl, 4-$CF_3$ | $C_6H_4$-4-$CF_3$ | m.p. 146° |
| 2.33 | — | 2-Cl, 4-$OCH_3$ | $C_6H_4$-4-$CF_3$ | m.p. 122° |
| 2.34 | — | 2,5-$(CH_3)_2$ | $C_6H_4$-4-$CF_3$ | m.p. 71° |
| 2.35 | — | 2-F, 5-$CH_3$ | $C_6H_4$-4-$CF_3$ | m.p. 133° |
| 2.36 | — | 2-F, 5-$CF_3$ | $C_6H_4$-4-$CF_3$ | m.p. 127° |
| 2.37 | — | 2,3,6-$F_3$ | $C_6H_4$-4-$CF_3$ | m.p. 150-1° |
| 2.38 | $CH_2CH_2$ | 2-Cl | $C_6H_5$ | m.p. 120-2° |
| 2.39 | $CH_2CH_2$ | 2-$CF_3$ | $C_6H_3$-2,3-$Cl_2$ | m.p. 128-30° |
| 2.40 | CH=CH | 2-Cl | $C_6H_4$-4-$CF_3$ | |
| 2.41 | CH=CH | 2-$CF_3$ | $C_6H_4$-2-$CF_3$ | m.p. 102-4° |
| 2.42 | 1,1-cyclobutyl | 2-Cl | $C_6H_4$-4-Cl | m.p. 104-7° |
| 2.43 | $CH_2CH_2CH_2$ | 2-$CF_3$ | $C_6H_5$ | m.p. 99-103° |

The compounds I according to the invention are notable for their broad activity spectrum and are valuable active ingredients in the field of pest control, including in particular the control of endoparasites, particularly helminths, on animals, whilst being well-tolerated by warm-blooded animals, fish and plants. These include the endoparasitic nematodes which may be the cause of serious diseases of mammals and poultry, e.g. sheep, pigs, goats, cattle, horses, donkeys, dogs, cats, guinea-pigs and exotic birds. Typical nematodes of this indication are: *Haemonchus, Trichostrongylus, Ostertagia, Nematodirus, Cooperia, Ascaris, Bunostonum, Oesophagostonum, Charbertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. The particular advantage of the compounds of formula I is their efficacy against those parasites that are resistant towards active ingredients based on benzimidazole.

Certain pests of the species *Nematodirus, Cooperia* and *Oesophagostonum* infest the intestinal tract of the host animal, while others of the species *Haemonchus* and *Ostertagia* are parasitic in the stomach and those of the species *Dictyocaulus* are parasitic in the lung tissue. Parasites of the families Filariidae and Setariidae may be found in the internal cell tissue and in the organs, e.g. the heart, the blood vessels, the lymph vessels and the subcutaneous tissue. A particularly notable parasite is the heartworm of the dog, *Dirofilaria immitis*. The compounds of formula I are highly effective against these parasites.

Furthermore, the compounds of formula I are suitable for the control of human pathogenic parasites. Of these, typical representatives that appear in the digestive tract are those of the species *Ancylostoma, Necator, Ascaris, Strongyloides, Trichinella, Capillaria, Trichuris* and *Enterobius*. The compounds of the present invention are also effective against parasites of the species *Wuchereria, Brugia, Onchocerca* and *Loa* from the family of Filariidae, which appear in the blood, in the tissue and in various organs, and also against Dracunculus and parasites of the species *Strongyloides* and *Trichinella*, which infect the gastrointestinal tract in particular.

The good pesticidal activity of the compounds of formula I corresponds to a mortality rate of at least 50-60% of the pests mentioned. In particular, the compounds of formula I are notable for the exceptionally long duration of efficacy.

The compounds of formula I are preferably employed in unmodified form or preferably together with the adjuvants conventionally used in the art of formulation and may therefore be processed in a known manner to give, for example, emulsifiable concentrates, directly dilutable solutions, dilute emulsions, soluble powders, granules or microencapsulations in polymeric substances. As with the compositions, the methods of application are selected in accordance with the intended objectives and the prevailing circumstances.

The formulation, i.e. the agents, preparations or compositions containing the active ingredient of formula I, or combinations of these active ingredients with other active ingredients, and optionally a solid or liquid adjuvant, are produced in a manner known per se, for example by intimately mixing and/or grinding the active ingredients with spreading compositions, for example with solvents, solid carriers, and optionally surface-active compounds (surfactants).

The solvents in question may be: alcohols, such as ethanol, propanol or butanol, and glycols and their ethers and esters, such as propylene glycol, dipropylene glycol ether, ethylene glycol, ethylene glycol monomethyl or -ethyl ether, ketones, such as cyclohexanone, isophorone or diacetanol alcohol, strong polar solvents, such as N-methyl-2-pyrrolidone, dimethyl sulfoxide or dimethylformamide, or water, vegetable oils, such as rape, castor, coconut, or soybean oil, and also, if appropriate, silicone oils.

Preferred application forms for usage on warm-blooded animals in the control of helminths include solutions, emulsions, suspensions (drenches), food additives, powders, tablets including effervescent tablets, boll, capsules, micro-capsules and pour-on formulations, whereby the physiological comparability of the formulation excipients must be taken into consideration.

The binders for tablets and boll may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), glidants and disintegrants.

If the anthelminthics are present in the form of feed concentrates, then the carriers used are e.g. performance feeds, feed grain or protein concentrates. Such feed concentrates or compositions may contain, apart from the active ingredients, also additives, vitamins, antibiotics, chemotherapeutics or other pesticides, primarily bacteriostats, fungistats, coccidiostats, or even hormone preparations, substances having anabolic action which promote growth, which affect the quality of meat of animals for slaughter or which are beneficial to the organism in another way. If the compositions or the active ingredients of formula I contained therein are added directly to feed or to the drinking troughs, then the formulated feed or drink contains the active ingredients preferably in a concentration of ca. 0.0005 to 0.02% by weight (5-200 ppm).

The compounds of formula I according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. If the range of activity is to be extended to endoparasites, e.g. wormers, the compounds of formula I are suitably combined with substances having endoparasitic properties. Of course, they can also be used in combination with antibacterial compositions. Since the compounds of formula I are adulticides, i.e. since they are effective in particular against the adult stage of the target parasites, the addition of pesticides which instead attack the juvenile stages of the parasites may be very advantageous. In this way, the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula I.

Suitable partners in the mixture may be biocides, e.g. the insecticides and acaricides with a varying mechanism of activity, which are named in the following and have been known to the person skilled in the art for a long time, e.g. chitin synthesis inhibitors, growth regulators; active ingredients which act as juvenile hormones; active ingredients which act as adulticides; broad-band insecticides, broad-band acaricides and nematicides; and also the well known anthelminthics and insect- and/or acarid-deterring substances, said repellents or detachers.

Non-limitative examples of suitable insecticides and acaricides are:

1. Abamectin
2. AC 303 630
3. Acephat
4. Acrinathrin
5. Alanycarb
6. Aldicarb
7. α-Cypermethrin
8. Alphamethrin
9. Amitraz
10. Avermectin $B_1$
11. AZ 60541
12. Azinphos A
13. Azinphos M
14. Azinphos-methyl
15. Azocyclotin
16. Bacillus subtil. toxin
17. Bendiocarb
18. Benfuracarb
19. Bensultap
20. β-Cyfluthrin
21. Bifenthrin
22. BPMC
23. Brofenprox
24. Bromophos A
25. Bufencarb
26. Buprofezin
27. Butocarboxin
28. Butylpyridaben
29. Cadusafos
30. Carbaryl
31. Carbofuran
32. Carbophenthion
33. Cartap
34. Chloethocarb
35. Chlorethoxyfos
36. Chlorfenapyr
37. Chlorfluazuron
38. Chlormephos
39. Chlorpyrifos
40. Cis-Resmethrin
41. Clocythrin
42. Clofentezin
43. Cyanophos
44. Cycloprothrin
45. Cyfluthrin
46. Cyhexatin
47. D 2341
48. Deltamethrin
49. Demeton M
50. Demeton S
51. Demeton-S-methyl
52. Dibutylaminothio
53. Dichlofenthion
54. Dicliphos
55. Diethion
56. Diflubenzuron
57. Dimethoat
58. Dimethylvinphos
59. Dioxathion
60. DPX-MP062
61. Edifenphos
62. Emamectin
63. Endosulfan
64. Esfenvalerat
65. Ethiofencarb
66. Ethion
67. Ethofenprox
68. Ethoprophos
69. Etrimphos
70. Fenamiphos
71. Fenazaquin
72. Fenbutatinoxid
73. Fenitrothion
74. Fenobucarb
75. Fenothiocarb
76. Fenoxycarb
77. Fenpropathrin
78. Fenpyrad
79. Fenpyroximate -continued 80. Fenthion
81. Fenvalerate
82. Fipronil
83. Fluazinam
84. Fluazuron
85. Flucycloxuron
86. Flucythrinat
87. Flufenoxuron
88. Flufenprox
89. Fonophos
90. Formothion
91. Fosthiazat
92. Fubfenprox
93. HCH
94. Heptenophos
95. Hexaflumuron
96. Hexythiazox
97. Hydroprene
98. Imidacloprid
99. Insekten-aktive Pilze
100. Insekten-aktive Nematoden
101. Insekten-aktive Viren
102. Iprobenfos
103. Isofenphos
104. Isoprocarb
105. Isoxathion
106. Ivermectin
107. λ-Cyhalothrin
108. Lufenuron
109. Malathion
110. Mecarbam
111. Mesulfenphos
112. Metaldehyd
113. Methamldophos
114. Methiocarb
115. Methomyl
116. Methoprene
117. Metolcarb
118. Mevinphos
119. Milbemectin
120. Moxidectin
121. Naled
122. NC 184
123. NI-25, Acetamiprid
124. Nitenpyram
125. Omethoat
126. Oxamyl
127. Oxydemethon M
128. Oxydeprofos
129. Parathion
130. Parathion-methyl
131. Permethrin
132. Phenthoat
133. Phorat
134. Phosalone
135. Phosmet
136. Phoxim
137. Pirimicarb
138. Pirimiphos A
139. Pirimiphos M
140. Promecarb
141. Propaphos
142. Propoxur
143. Prothiofos
144. Prothoat
145. Pyrachlophos
146. Pyradaphenthion
147. Pyresmethrin
148. Pyrethrum
149. Pyridaben
150. Pyrimidifen
151. Pyriproxyfen
152. RH 5992
153. RH-2485
154. Salithion
155. Sebufos
156. Silafluofen
157. Spinosad
158. Sulfotep -continued 159. Sulprofos
160. Tebufenozide
161. Tebufenpyrad
162. Tebupirimphos
163. Teflubenzuron
164. Tefluthrin
165. Temephos
166. Terbam
167. Terbufos
168. Tetrachlorvinphos
169. Thiafenox
170. Thiodicarb
171. Thiofanox
172. Thionazin
173. Thuringiensin
174. Tralomethrin
175. Triarthen
176. Triazamate
177. Triazophos
178. Triazuron
179. Trichlorfon
180. Triflumuron
181. Trimethacarb
182. Vamidothion
183. XMC (3,5,-Xy-lylmethylcarbamat)
184. Xylylcarb
185. YI 5301/5302
186. ζ-Cypermethrin
187. Zetamethrin Non-limitative examples of suitable anthelminthics are named in the following, a few representatives have insecticidal and acaricidal activity in addition to the anthelminthic activity, and are partly already in the above list.

(A1) Praziquantel=2-cyclohexylcarbonyl-4-oxo-1,2,3,6,7,11b-hexahydro-4H-pyrazino[2,1-α]isoquinoline (A2) Closantel=3,5-diiodo-N-[5-chloro-2-methyl-4-(a-cyano-4-chlorobenzyl)phenyl]-salicylamide (A3) Triclabendazole=5-chloro-6-(2,3-dichlorophenoxy)-2-methylthio-1H-benzimidazole (A4) Levamisol=L-(−)-2,3,5,6-tetrahydro-6-phenylimidazo[2,1b]thiazole (A5) Mebendazole=(5-benzoyl-1H-benzimidazol-2-yl)carbaminic acid methylester (A6) Omphalotin=a macrocyclic fermentation product of the fungus *Omphalotus oleanus* described in WO 97/20857

(A7) Abamectin=avermectin B1

(A8) Ivermectin=22,23-dihydroavermectin B1

(A9) Moxidectin 5-O-demethyl-28-deoxy-25-(1,3-dimethyl-1-butenyl)-6,28-epoxy-23-(methoxyimino)-milbemycin B (A10) Doramectin=25-cyclohexyl-5-O-demethyl-25-de(1-methylpropyl)-avermectin A1a (A11) Milbemectin=mixture of milbemycin A3 and milbemycin A4

(A12) Milbemycinoxim=5-oxime of milbemectin

Non-limitative examples of suitable repellents and detachers are:

(R1) DEET (N,N-diethyl-m-toluamide)

(R2) KBR 3023 N-butyl-2-oxycarbonyl-(2-hydroxy)-piperidine (R3) Cymiazole=N,-2,3-dihydro-3-methyl-1,3-thiazol-2-ylidene-2,4-xylidene The said partners in the mixture are best known to specialists in this field. Most are described in various editions of the Pesticide Manual, The British Crop Protection Council, London, and others in the various editions of The Merck Index, Merck & Co., Inc., Rahway, N.J., USA or in patent literature.

Therefore, the following listing is restricted to a few places where they may be found by way of example.

(I) 2-Methyl-2-(methylthio)propionaldehyde-O-methylcarbamoyloxime (Aldicarb), from The Pesticide Manual, 11$^{th}$ Ed. (1997), The British Crop Protection Council, London, page 26;

(II) S-(3,4-dihydro-4-oxobenzo[d]-[1,2,3]-triazin-3-ylmethyl)O,O-dimethyl-phosphoro-dithioate (Azinphos-methyl), from The Pesticide Manual, 11$^{th}$ Ed. (1997), The British Crop Protection Council, London, page 67;

(III) Ethyl-N-[2,3-dihydro-2,2-dimethylbenzofuran-7-yloxycarbonyl-(methyl)aminothio]-N-isopropyl-β-alaninate (Benfuracarb), from The Pesticide Manual, 11$^{th}$ Ed. (1997), The British Crop Protection Council, London, page 96;

(IV) 2-Methylbiphenyl-3-ylmethyl-(Z)-(1RS)-cis-3-(2-chloro-3,3,3-trifluoroprop-1-enyl)-2,2-dimethylcyclopropanecarboxylate (Bifenthrin), from The Pesticide Manual, 11$^{th}$ Ed. (1997), The British Crop Protection Council, London, page 118;

(V) 2-tert-butylimino-3-isopropyl-5-phenyl-1,3,5-thiadiazian-4-one (Buprofezin), from The Pesticide Manual, 11$^{th}$ Ed. (1997), The British Crop Protection Council, London, page 157;

(VI) 2,3-Dihydro-2,2-dimethylbenzofuran-7-yl-methylcarbamate (Carbofuran), from The Pesticide Manual, 11$^{th}$ Ed. (1997), The British Crop Protection Council, London, page 186;

(VII) 2,3-Dihydro-2,2-dimethylbenzofuran-7-yl-(dibutylaminothio)methylcarbamate (Carbosulfan), from The Pesticide Manual, 11$^{th}$ Ed. (1997), The British Crop Protection Council, London, page 188;

(VIII) S,S'-(2-dimethylaminotrimethylene)-bis(thiocarbamate) (Cartap), from The Pesticide Manual, 11$^{th}$ Ed. (1997), The British Crop Protection Council, London, page 193;

(IX) 1-[3,5-Dichloro-4-(3-chloro-5-trifluoromethyl-2-pyridyloxy)phenyl]-3-(2,6-difluoro-benzoyl)-urea (Chlorfluazuron), from The Pesticide Manual, 11$^{th}$ Ed. (1997), The British Crop Protection Council, London, page 213;

(X) O,O-diethyl-O-3,5,6-trichloro-2-pyridyl-phosphorothioate (Chlorpyrifos), from The Pesticide Manual, 11$^{th}$ Ed. (1997), The British Crop Protection Council, London, page 235;

(XI) (RS)-α-cyano-4-fluoro-3-phenoxybenzyl-(1RS,3RS1RS,3RS)-3-(2,2-dichlorovinyl)2,2-di-methylcyclopropanecarboxylate (Cyfluthrin), from The Pesticide Manual, 11$^{th}$ Ed. (1997), The British Crop Protection Council, London, page 293;

(XII) Mixture of (S)-α-cyano-3-phenoxybenzyl-(Z)-(1R,3R)-3-(2-chloro-3,3,3-trifluoro-propenyl)-2,2-dimethyl-cyclopropanecarboxylate and (R)-α-cyano-3-phenoxybenzyl-(Z)-(1R,3R)-3-(2-chloro-3,3,3-trifluoropropenyl)-2,2-dimethylcyclopropanecarboxylate (Lambda-Cyhalothrin), from The Pesticide Manual, 11$^{th}$ Ed. (1997), The British Crop Protection Council, London, page 300;

(XIII) Racemate consisting of (S)-α-cyano-3-phenoxybenzyl-(Z)-(1R,3R)-3-(2,2-dichlorovinyl)-2,2-dimethylcyclopropanecarboxylate and (R)-α-cyano-3-phenoxybenzyl-(1S,3S)-3-(2,2-dichlorovinyl)-2,2-dimethylcyclopropanecarboxylate (Alpha-cypermethrin), from The Pesticide Manual, 11$^{th}$ Ed. (1997), The British Crop Protection Council, London, page 308;

(XIV) a mixture of the stereoisomers of (S)-α-cyano-3-phenoxybenzyl (1RS,3RS,1RS,3RS)-3-(2,2-dichlorovinyl)-2,2-dimethylcyclopropanecarboxylate (zeta-Cypermethrin), from The Pesticide Manual, 11$^{th}$ Ed. (1997), The British Crop Protection Council, London, page 314;

(XV) (S)-α-cyano-3-phenoxybenzyl-(1R,3R)-3-(2,2-dibromovinyl)-2,2-dimethylcyclopropane-carboxylate (Deltamethrin), from The Pesticide Manual, 11$^{th}$ Ed. (1997), The British Crop Protection Council, London, page 344;

(XVI) (4-chlorophenyl)-3-(2,6-difluorobenzoyl)urea (Diflubenzuron), from The Pesticide Manual, 11$^{th}$ Ed. (1997), The British Crop Protection Council, London, page 395;

(XVII) (1,4,5,6,7,7-Hexachloro-8,9,10-trinorborn-5-en-2,3-ylenebismethylene)-sulphite (Endosulfan), from The Pesticide Manual, 11$^{th}$ Ed. (1997), The British Crop Protection Council, London, page 459;

(XVIII) α-ethylthio-o-tolyl-methylcarbamate (Ethiofencarb), from The Pesticide Manual, 11$^{th}$ Ed. (1997), The British Crop Protection Council, London, page 479;

(XIX) O,O-dimethyl-O-4-nitro-m-tolyl-phosphorothioate (Fenitrothion), from The Pesticide Manual, 11$^{th}$ Ed. (1997), The British Crop Protection Council, London, page 514;

(XX) 2-sec-butylphenyl-methylcarbamate (Fenobucarb), from The Pesticide Manual, 11$^{th}$ Ed. (1997), The British Crop Protection Council, London, page 516;

(XXI) (RS)-α-cyano-3-phenoxybenzyl-(RS)-2-(4-chlorophenyl)-3-methylbutyrate (Fenvalerate), from The Pesticide Manual, 11$^{th}$ Ed. (1997), The British Crop Protection Council, London, page 539;

(XXII) S-[formyl(methyl)carbamoylmethyl]-O,O-dimethyl-phosphorodithioate (Formothion), from The Pesticide Manual, 11$^{th}$ Ed. (1997), The British Crop Protection Council, London, page 625;

(XXIII) 4-Methylthio-3,5-xylyl-methylcarbamate (Methiocarb), from The Pesticide Manual, 11$^{th}$ Ed. (1997), The British Crop Protection Council, London, page 813;

(XXIV) 7-Chlorobicyclo[3.2.0]hepta-2,6-dien-6-yl-dimethylphosphate (Heptenophos), from The Pesticide Manual, 11$^{th}$ Ed. (1997), The British Crop Protection Council, London, page 670;

(XXV) 1-(6-chloro-3-pyridylmethyl)-N-nitroimidazolidin-2-ylidenamine (Imidacloprid), from The Pesticide Manual, 11$^{th}$ Ed. (1997), The British Crop Protection Council, London, page 706;

(XXVI) 2-isopropylphenyl-methylcarbamate (Isoprocarb), from The Pesticide Manual, 11$^{th}$ Ed. (1997), The British Crop Protection Council, London, page 729;

(XXVII) O,S-dimethyl-phosphoramidothioate (Methamidophos), from The Pesticide Manual, 11$^{th}$ Ed. (1997), The British Crop Protection Council, London, page 808;

(XXVIII) S-Methyl-N-(methylcarbamoyloxy)thioacetimidate (Methomyl), from The Pesticide Manual, 11$^{th}$ Ed. (1997), The British Crop Protection Council, London, page 815;

(XXIX) Methyl-3-(dimethoxyphosphinoyloxy)but-2-enoate (Mevinphos), from The Pesticide Manual, 11$^{th}$ Ed. (1997), The British Crop Protection Council, London, page 844;

(XXX) O,O-diethyl-O-4-nitrophenyl-phosphorothioate (Parathion), from The Pesticide Manual, 11$^{th}$ Ed. (1997), The British Crop Protection Council, London, page 926;

(XXXI) O,O-dimethyl-O-4-nitrophenyl-phosphorothioate (Parathion-methyl), from The Pesticide Manual, 11$^{th}$ Ed. (1997), The British Crop Protection Council, London, page 928;

(XXXII) S-6-chloro-2,3-dihydro-2-oxo-1,3-benzoxazol-3-ylmethyl-O,O-diethyl-phosphor-dithioate (Phosalone), from The Pesticide Manual, 11$^{th}$ Ed. (1997), The British Crop Protection Council, London, page 963;

(XXXIII) 2-Dimethylamino-5,6-dimethylpyrimidin-4-yl-dimethylcarbamate (Pirimicarb), from The Pesticide Manual, 11$^{th}$ Ed. (1997), The British Crop Protection Council, London, page 985;

(XXXIV) 2-isopropoxyphenyl-methylcarbamate (Propoxur), from The Pesticide Manual, 11$^{th}$ Ed. (1997), The British Crop Protection Council, London, page 1036;

(XXXV) 1-(3,5-dichloro-2,4-difluorophenyl)-3-(2,6-difluorobenzoyl)urea (Teflubenzuron), from The Pesticide Manual, 11$^{th}$ Ed. (1997), The British Crop Protection Council, London, page 1158;

(XXXVI) S-tert-butylthiomethyl-O,O-dimethyl-phosphorodithioate (Terbufos), from The Pesticide Manual, 11$^{th}$ Ed. (1997), The British Crop Protection Council, London, page 1165;

(XXXVII) ethyl-(3-tert.-butyl-1-dimethylcarbamoyl-1H-1,2,4-triazol-5-yl-thio)-acetate, (Triazamate), from The Pesticide Manual, 11$^{th}$ Ed. (1997), The British Crop Protection Council, London, page 1224;

(XXXVIII) Abamectin, from The Pesticide Manual, 11$^{th}$ Ed. (1997), The British Crop Protection Council, London, page 3;

(XXXIX) 2-sec-butylphenyl-methylcarbamate (Fenobucarb), from The Pesticide Manual, 11$^{th}$ Ed. (1997), The British Crop Protection Council, London, page 516;

(XL) N-tert.-butyl-N'-(4-ethylbenzoyl)-3,5-dimethylbenzohydrazide (Tebufenozide), from The Pesticide Manual, 11$^{th}$ Ed. (1997), The British Crop Protection Council, London, page 1147;

(XLI) (±)-5-amino-1-(2,6-dichloro α,α,α-4-trifluoro-p-tolyl)4-trifluoromethyl-sulphinylpyrazol-3-carbonitrile (Fipronil), from The Pesticide Manual, 11$^{th}$ Ed. (1997), The British Crop Protection Council, London, page 545;

(XLII) (RS)-α-cyano-4-fluoro-3-phenoxybenzyl(1RS,3RS,1RS,3RS)3-(2,2-dichlorovinyl)-2,2-dimethylcyclopropanecarboxylate (beta-Cyfluthrin), from The Pesticide Manual, 11$^{th}$ Ed. (1997), The British Crop Protection Council, London, page 295;

(XLIII) (4-ethoxyphenyl)-[3-(4-fluoro-3-phenoxyphenyl)propyl](dimethyl)silane (Silafluofen), from The Pesticide Manual, 11$^{th}$ Ed. (1997), The British Crop Protection Council, London, page 1105;

(XLIV) tert.-butyl (E)-α-(1,3-dimethyl-5-phenoxypyrazol-4-yl-methylenamino-oxy)-p-toluate (Fenpyroximate), from The Pesticide Manual, 11$^{th}$ Ed. (1997), The British Crop Protection Council, London, page 530;

(XLV) 2-tert.-butyl-5-(4-tert.-butylbenzylthio)-4-chloropyridazin-3(2H)-one (Pyridaben), from The Pesticide Manual, 11$^{th}$ Ed. (1997), The British Crop Protection Council, London, page 1161;

(XLVI) 4-[[4-(1,1-dimethylphenyl)phenyl]ethoxy]-quinazoline (Fenazaquin), from The Pesticide Manual, 11$^{th}$ Ed. (1997), The British Crop Protection Council, London, page 507;

(XLVII) 4-phenoxyphenyl-(RS)-2-(pyridyloxy)propyl-ether (Pyriproxyfen), from The Pesticide Manual, 11$^{th}$ Ed. (1997), The British Crop Protection Council, London, page 1073;

(XLVIII) 5-chloro-N-{2-[4-(2-ethoxyethyl)-2,3-dimethylphenoxy]ethyl}-6-ethylpyrimidine-4-amine (Pyrimidifen), from The Pesticide Manual, 11$^{th}$ Ed. (1997), The British Crop Protection Council, London, page 1070;

(XLIX) (E)-(6-chloro-3-pyridylmethyl)-N-ethyl-N'-methyl-2-nitrovinylidenediamine (Nitenpyram), from The Pesticide Manual, 11$^{th}$ Ed. (1997), The British Crop Protection Council, London, page 880;

(L) (E)-N$^1$-[(6-chloro-3-pyridyl)methyl]-N$^2$-cyano-N$^1$-methylacetamidine (NI-25, Acetamiprid), from The Pesticide Manual, 11$^{th}$ Ed. (1997), The British Crop Protection Council, London, page 9;

(LI) Avermectin B$_1$, from The Pesticide Manual, 11$^{th}$ Ed. (1997), The British Crop Protection Council, London, page 3;

(LII) an insect-active extract from a plant, especially (2R,6aS,12aS)-1,2,6,6a,12,12a-hexhydro-2-isopropenyl-8,9-dimethoxy-chromeno[3,4-b]furo[2,3-h]chromen-6-one (Rotenone), from The Pesticide Manual, 11$^{th}$ Ed. (1997), The British Crop Protection Council, London, page 1097; and an extract from *Azadirachta indica*, especially azadirachtin, from The Pesticide Manual, 11$^{th}$ Ed. (1997), The British Crop Protection Council, London, page 59; and (LIII) a preparation which contains insect-active nematodes, preferably *Heterorhabditis bacteriophora* and *Heterorhabditis megidis*, from The Pesticide Manual, 11$^{th}$ Ed. (1997), The British Crop Protection Council, London, page 671; *Steinemema feltiae*, from The Pesticide Manual, 11$^{th}$ Ed. (1997), The British Crop Protection Council, London, page 1115 and *Steinemema scapterisci*, from The Pesticide Manual, 11$^{th}$ Ed. (1997), The British Crop Protection Council, London, page 1116;

(LIV) a preparation obtainable from *Bacillus subtilis*, from The Pesticide Manual, 11$^{th}$ Ed. (1997), The British Crop Protection Council, London, page 72; or from a strain of *Bacillus thuringiensis* with the exception of compounds isolated from GC91 or from NCTC11821; The Pesticide Manual, 11$^{th}$ Ed. (1997), The British Crop Protection Council, London, page 73;

(LV) a preparation which contains insect-active fungi, preferably *Verticillium lecanii*, from The Pesticide Manual, 11$^{th}$ Ed. (1997), The British Crop Protection Council, London, page 1266; *Beauveria brogniartii*, from The Pesticide Manual, 11$^{th}$ Ed. (1997), The British Crop Protection Council, London, page 85 and *Beauveria bassiana*, from The Pesticide Manual, 11$^{th}$ Ed. (1997), The British Crop Protection Council, London, page 83;

(LVI) a preparation which contains insect-active viruses, preferably *Neodipridon Sertifer* NPV, from The Pesticide Manual, 11$^{th}$ Ed. (1997), The British Crop Protection Council, London, page 1342; *Mamestra brassicae* NPV, from The Pesticide Manual, 11$^{th}$ Ed. (1997), The British Crop Protection Council, London, page 759 and *Cydia pomonella* granulosis virus, from The Pesticide Manual, 11$^{th}$ Ed. (1997), The British Crop Protection Council, London, page 291;

(CLXXXI) 7-chloro-2,3,4a,5-tetrahydro-2-[methoxycarbonyl(4-trifluoromethoxyphenyl)-carbamoyl]indol[1,2e]oxazoline-4a-carboxylate (DPX-MP062, Indoxycarb), from The Pesticide Manual, 11$^{th}$ Ed. (1997), The British Crop Protection Council, London, page 453;

(CLXXXII) N'-tert.-butyl-N'-(3,5-dimethylbenzoyl)-3-methoxy-2-methylbenzohydrazide (RH-2485, Methoxyfenozide), from The Pesticide Manual, 11$^{th}$ Ed. (1997), The British Crop Protection Council, London, page 1094; and (CLXXXIII) (N'L[methoxy-biphenyl-3-yl]-hydrazinecarboxylic acid isopropylester (D 2341), from Brighton Crop Protection Conference, 1996, 487-493;

(R2) Book of Abstracts, 212th ACS National Meeting Orlando, Fla., August 25-29 (1996), AGRO-020. Publisher American Chemical Society, Washington, D.C. CONEN: 63BFAF.

As a consequence of the above details, a further essential aspect of the present invention relates to combination preparations for the control of parasites on warm-blooded animals, characterised in that they contain, in addition to a compound of formula I, at least one further active ingredient having the same or different sphere of activity and at least one physiologically acceptable carrier. The present invention is not restricted to two-fold combinations.

As a rule, the anthelmintic compositions according to the invention contain 0.1 to 99% by weight, especially 0.1 to 95% by weight of active ingredient of formula I, Ia or mixtures thereof, 99.9 to 1% by weight, especially 99.8 to 5% by weight of a solid or liquid admixture, including 0 to 25% by weight, especially 0.1 to 25% by weight of a surfactant.

Application of the compositions according to the invention to the animals to be treated may take place topically, per-orally, parenterally or subcutaneously, the composition being present in the form of solutions, emulsions, suspensions, (drenches), powders, tablets, boli, capsules and pour-on formulations.

The pour-on or spot-on method consists in applying the compound of formula I to a specific location of the skin or coat, advantageously to the neck or backbone of the animal. This takes place e.g. by applying a swab or spray of the pour-on or spot-on formulation to a relatively small area of the coat, from where the active substance is dispersed almost automatically over wide areas of the fur owing to the spreading nature of the components in the formulation and assisted by the animal's movements.

Pour-on or spot-on formulations suitably contain carriers, which promote rapid dispersement over the skin surface or in the coat of the host animal, and are generally regarded as spreading oils. Suitable carriers are e.g. oily solutions; alcoholic and isopropanolic solutions such as solutions of 2-octyldodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, capric acid esters of saturated fat alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or also solutions of esters of aliphatic acids, e.g. glycols. It may be advantageous for a dispersing agent to be additionally present, such as one known from the pharmaceutical or cosmetic industry. Examples are 2-pyrrolidone, 2-(N-alkyl)pyrrolidone, acetone, polyethylene glycol and the ethers and esters thereof, propylene glycol or synthetic triglycerides.

The oily solutions include e.g. vegetable oils such as olive oil, groundnut oil, sesame oil, pine oil, linseed oil or castor oil. The vegetable oils may also be present in epoxidised form. Paraffins and silicone oils may also be used.

A pour-on or spot-on formulation generally contains 1 to 20% by weight of a compound of formula I, 0.1 to 50% by weight of dispersing agent and 45 to 98.9% by weight of solvent.

The pour-on or spot-on method is especially advantageous for use on herd animals such as cattle, horses, sheep or pigs, in which it is difficult or time-consuming to treat all the animals orally or by injection. Because of its simplicity, this method can of course also be used for all other animals, including individual domestic animals or pets, and is greatly favoured by the keepers of the animals, as it can often be carried out without the specialist presence of the veterinarian.

Whereas it is preferred to formulate commercial products as concentrates, the end user will normally use dilute formulations.

Such compositions may also contain further additives, such as stabilisers, anti-foaming agents, viscosity regulators, binding agents or tackifiers, as well as other active ingredients, in order to achieve special effects.

Anthelminthic compositions of this type, which are used by the end user, similarly form a constituent of the present invention.

In each of the processes according to the invention for pest control or in each of the pest control compositions according to the invention, the active ingredients of formula I can be used in all of their steric configurations or in mixtures thereof.

The invention also includes a method of prophylactically protecting warm-blooded animals, especially productive livestock, domestic animals and pets, against parasitic helminths, which is characterised in that the active ingredients of formula I or the active ingredient formulations prepared therefrom are administered to the animals as an additive to the feed, or to the drinks or also in solid or liquid form, orally or by injection or parenterally. The invention also includes the compounds of formula I according to the invention for usage in one of the said processes.

The following examples serve merely to illustrate the invention without restricting it, the term active ingredient representing a substance listed in tables 1 to 3.

In particular, preferred formulations are made up as follows:

(%=percent by weight)

FORMULATION EXAMPLES

|  | a) | b) |
| --- | --- | --- |
| active ingredient from tables 1 and 2 | 5% | 10% |
| kaolin | 94% | — |
| highly dispersed silicic acid | 1% | — |
| attapulgite | — | 90% |

The active ingredient is dissolved in methylene chloride, sprayed onto the carrier and the solvent subsequently concentrated by evaporation under vacuum. Granulates of this kind can be mixed with the animal feed.

2. Granulate

| | |
| --- | --- |
| active ingredient from tables 1 and 2 | 3% |
| polyethylene glycol (mw 200) | 3% |
| kaolin | 94% |
| (mw = molecular weight) | |

The finely ground active ingredient is evenly applied in a mixer to the kaolin which has been moistened with polyethylene glycol. In this way, dust-free coated granules are obtained.

3. Tablets or Boli

| | | |
| --- | --- | --- |
| I | active ingredient from tables 1 and 2 | 33.00% |
| | methylcellulose | 0.80% |
| | silicic acid, highly dispersed | 0.80% |
| | corn starch | 8.40% |
| II | lactose, cryst. | 22.50% |
| | corn starch | 17.00% |
| | microcryst. cellulose | 16.50% |
| | magnesium stearate | 1.00% |

I Methyl cellulose is stirred into water. After the material has swollen, silicic acid is stirred in and the mixture homogeneously suspended. The active ingredient and the corn starch are mixed. The aqueous suspension is worked into this mixture and kneaded to a dough. The resulting mass is granulated through a 12 M sieve and dried.

II All 4 excipients are mixed thoroughly.

III The preliminary mixes obtained according to I and II are mixed and pressed into tablets or boli.

4. Injectables

A. Oily Vehicle (Slow Release)

| | | |
|---|---|---|
| 1. | active ingredient from tables 1 and 2 | 0.1-1.0 g |
| | groundnut oil | ad 100 ml |
| 2. | active ingredient from tables 1 and 2 | 0.1-1.0 g |
| | sesame oil | ad 100 ml |

Preparation: The active ingredient is dissolved in part of the oil whilst stirring and, if required, with gentle heating, then after cooling made up to the desired volume and sterile-filtered through a suitable membrane filter with a pore size of 0.22 mm.

B Water-Miscible Solvent (Average Rate of Release)

| | |
|---|---|
| active ingredient from tables 1 and 2 | 0.1-1.0 g |
| 4-hydroxymethyl-1,3-dioxolane (glycerol formal) | 40 g |
| 1,2-propanediol | ad 100 ml |
| An active ingredient from table 1 | 0.1-1.0 g |
| glycerol dimethyl ketal | 40 g |
| 1,2-propanediol | ad 100 ml |

Preparation: The active ingredient is dissolved in part of the solvent whilst stirring, made up to the desired volume and sterile-filtered through a suitable membrane filter with a pore size of 0.22 mm.

C. Aqueous Solubilisate (Rapid Release)

| | | |
|---|---|---|
| 1. | active ingredient from tables 1 and 2 | 0.1-1.0 g |
| | polyethoxylated castor oil (40 ethylene oxide units) | 10 g |
| | 1,2-propanediol | 20 g |
| | benzyl alcohol | 1 g |
| | aqua ad inject. | ad 100 ml |
| 2. | active ingredient from tables 1 and 2 | 0.1-1.0 g |
| | polyethoxylated sorbitan monooleat (20 ethylene oxide units) | 8 g |
| | 4-hydroxymethyl-1,3-dioxolane (glycerol formal) | 20 g |
| | benzyl alcohol | 1 g |
| | aqua ad inject. | ad 100 ml |

Preparation: The active ingredient is dissolved in the solvents and the surfactant, and made up with water to the desired volume. Sterile filtration through an appropriate membrane filter of 0.22 mm pore size.

5. Pour On

| A. | |
|---|---|
| active ingredient from tables 1 and 2 | 5 g |
| isopropyl myristate | 10 g |
| isopropanol | ad 100 ml |

-continued

| B | |
|---|---|
| active ingredient from tables 1 and 2 | 2 g |
| hexyl laurate | 5 g |
| medium-chained triglyceride | 15 g |
| ethanol | ad 100 ml |
| C. | |
| active ingredient from tables 1 and 2 | 2 g |
| oleyl oleate | 5 g |
| N-methylpyrrolidone | 40 g |
| isopropanol | ad 100 ml |

The aqueous systems may also preferably be used for oral and/or intraruminal application.

The compositions may also contain further additives, such as stabilisers, e.g. where appropriate epoxidised vegetable oils (epoxidised coconut oil, rapeseed oil, or soybean oil); antifoams, e.g. silicone oil, preservatives, viscosity regulators, binders, and tackifiers, as well as fertilisers or other active ingredients to achieve special effects.

Further biologically active substances or additives, which are neutral towards the compounds of formula I and do not have a harmful effect on the host animal to be treated, as well as mineral salts or vitamins, may also be added to the described compositions.

Biological Examples

1. In-vivo test on *Trichostrongylus colubriformis* and *Haemonchus contortus* on Mongolian Gerbils (*Meriones unguiculatus*) Using Peroral Application Six to eight week old Mongolian gerbis are infected by artificial feeding with ca. 2000 third instar larvae each of *T. colubriformis* and *H. contortus.* 6 days after infection, the gerbils are lightly anaesthetised with $N_2O$ and treated by peroral application with the test compounds, dissolved in a mixture of 2 parts DMSO and 1 part polyethylene glycol (PEG 300), in quantities of 100, 32 and 10-0.1 mg/kg. On day 9 (3 days after treatment), when most of the *H. contortus* that are still present are late 4th instar larvae and most of the *T. colubriformis* are immature adults, the gerbils are killed in order to count the worms. The efficacy is calculated as the % reduction of the number of worms in each gerbil, compared with the geometric average of number of worms from 8 infected and untreated gerbils.

In this test, a vast reduction in nematode infestation is achieved with compounds of formula I.

What is claimed is:

1. A method of controlling *Haemonchus contortus* and *Trichostrongylus colubriformis* helminthes in warm-blooded domestic animals comprising administering a composition to said domestic animals, wherein said composition comprises a pesticidically active amount of the compound of the formula 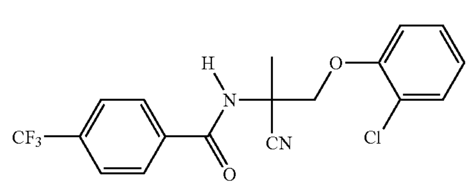 and optionally enantiomers thereof.

2. A method of controlling helminthes in domestic animals comprising administering a composition to said domestic animals, wherein said composition comprises a pesticidally active amount of a compound of the formula

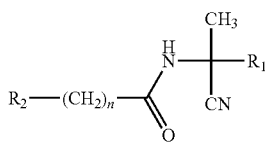

wherein
$R_2$ signifies unsubstituted phenyl or phenyl mono- or disubstituted by $R_5$;
n is 0 or 1;
$R_1$ is methylene which is substituted by unsubstituted phenyloxy or phenyloxy mono- or disubstituted by $R_5$, whereby the substituents may be the same as one another or different if the number thereof is greater than 1; and
$R_5$ signifies halogen-$C_1$-$C_6$-alkyl, halogen-$C_1$-$C_6$-alkenyl, halogen-$C_1$-$C_6$-alkynyl, or halogen.

3. The method of claim 2 wherein said helminthes are endoparasitic nematodes.

4. The method of claim 3 wherein said endoparasitic nematodes are selected from the group consisting of *Haemonchus, Trichostrongylus, Ostertagia, Nematodirus, Cooperia, Ascaris, Bunostonum, Oesophagostonum, Charbertia, Trichuris, Strongylus, Trichonema, Dictyocaulus, Capillaria, Heterakis, Toxocara, Ascaridia, Oxyuris, Ancylostoma, Uncinaria, Toxascaris*, and *Paracaris*.

* * * * *